US011045407B2

(12) United States Patent
Baghdadli

(10) Patent No.: US 11,045,407 B2
(45) Date of Patent: *Jun. 29, 2021

(54) PROCESS FOR TREATING KERATIN FIBRES WITH A PYRIDINEDICARBOXYLIC ACID COMPOUND

(71) Applicant: L'OREAL, Paris (FR)

(72) Inventor: Nawel Baghdadli, Massy (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/021,452

(22) PCT Filed: Sep. 11, 2014

(86) PCT No.: PCT/EP2014/069383
§ 371 (c)(1),
(2) Date: Mar. 11, 2016

(87) PCT Pub. No.: WO2015/036477
PCT Pub. Date: Mar. 19, 2015

(65) Prior Publication Data
US 2016/0213587 A1    Jul. 28, 2016

(30) Foreign Application Priority Data

Sep. 12, 2013   (FR) ...................... 1358764

(51) Int. Cl.
| *A61K 8/49* | (2006.01) |
| *A45D 2/00* | (2006.01) |
| *A61Q 5/06* | (2006.01) |
| *A61Q 5/12* | (2006.01) |
| *A61Q 5/00* | (2006.01) |

(52) U.S. Cl.
CPC ............ *A61K 8/4926* (2013.01); *A45D 2/001* (2013.01); *A61Q 5/002* (2013.01); *A61Q 5/12* (2013.01); *A61Q 5/06* (2013.01)

(58) Field of Classification Search
None
See application file for complete search history.

(56) References Cited

U.S. PATENT DOCUMENTS

| 4,185,087 A | 1/1980 | Morlino |
| 4,452,261 A | 6/1984 | Bresak et al. |
| 4,717,727 A | 1/1988 | Gunzler et al. |
| 4,770,873 A | 9/1988 | Wolfram et al. |
| 5,004,748 A | 4/1991 | Baader et al. |
| 5,046,516 A | 9/1991 | Barradas |
| 5,143,926 A | 9/1992 | Baader et al. |
| 5,356,909 A | 10/1994 | Baader et al. |
| 5,618,523 A | 4/1997 | Zysman et al. |
| 5,665,778 A | 9/1997 | Semeria et al. |
| 5,773,611 A | 6/1998 | Zysman et al. |
| 5,957,140 A | 9/1999 | McGee |
| 5,959,127 A | 9/1999 | Semeria et al. |
| 5,992,425 A | 11/1999 | Teratani et al. |
| 6,110,450 A | 8/2000 | Bergmann |
| 6,595,861 B1 | 7/2003 | Morrow et al. |
| 8,163,273 B2 | 4/2012 | Devin-Baudoin et al. |
| 2002/0082399 A1 | 6/2002 | Kuzee et al. |
| 2002/0172653 A1 | 11/2002 | Cannell et al. |
| 2002/0187117 A1 | 12/2002 | Devin-Baudoin et al. |
| 2002/0193264 A1 | 12/2002 | Cannell et al. |
| 2003/0053977 A1 | 3/2003 | Cannell et al. |
| 2003/0223945 A1 | 12/2003 | Dalko et al. |
| 2005/0013786 A1 | 1/2005 | Sabbagh et al. |
| 2005/0227902 A1 | 10/2005 | Erazo-Majewicz et al. |
| 2008/0226576 A1 | 9/2008 | Benabdillah et al. |
| 2009/0044823 A1 | 2/2009 | Overend et al. |
| 2009/0215837 A1 | 8/2009 | Dalko et al. |
| 2010/0016886 A1 | 1/2010 | Lu |
| 2010/0105741 A1 | 4/2010 | Dalko et al. |
| 2010/0263683 A1 | 10/2010 | Dutheil-Gouret et al. |
| 2011/0020258 A1 | 1/2011 | Lorant |
| 2011/0150812 A1 | 6/2011 | Mecca |
| 2011/0224724 A1 | 9/2011 | Lu et al. |
| 2011/0268681 A1 | 11/2011 | Gonzalez et al. |
| 2013/0131095 A1 | 5/2013 | Dalko et al. |
| 2014/0076346 A1 | 3/2014 | Bourdin et al. |

FOREIGN PATENT DOCUMENTS

| EP | 0095238 A2 | 11/1983 |
| EP | 0176741 A1 | 4/1986 |
| EP | 0217635 A2 | 4/1987 |
| EP | 0281943 A2 | 9/1988 |
| EP | 0500437 A1 | 8/1992 |
| EP | 0530974 A1 | 3/1993 |

(Continued)

OTHER PUBLICATIONS

Translation of Jegou et al. FR 2944967, accessed Nov. 21, 2016.*
Anna K. Fryxell. "Get Your Straightest Hair Ever With These Tools" <https://www.newbeauty.com/blog/dailybeauty/6572-final-get-your-straightest-hair-ever-with-these-tools/> Aug. 31, 2012 (Year: 2012).*
International Search Report for PCT/EP2014/069377, dated Jan. 22, 2015.
International Search Report for PCT/EP2014/069378, dated Jan. 21, 2015.
International Search Report for PCT/EP2014/069380, dated Jan. 22, 2015.
International Search Report for PCT/EP2014/069381, dated Feb. 13, 2015.
International Search Report for PCT/EP2014/069383, dated Feb. 11, 2015.

(Continued)

*Primary Examiner* — Nicole P Babson
(74) *Attorney, Agent, or Firm* — The Marbury Law Group, PLLC

(57) ABSTRACT

The invention relates to a process for treating keratin fibres, in particular human keratin fibres such as the hair, comprising the application to the keratin fibres of a cosmetic composition comprising a pyridinedicarboxylic acid compound. The process makes it possible to obtain good cosmetic properties in terms of manageability of the hair and sheen, with a long-lasting effect.

14 Claims, No Drawings

(56) References Cited

FOREIGN PATENT DOCUMENTS

| | | | |
|---|---|---|---|
| EP | 0647617 | A1 | 4/1995 |
| EP | 1352629 | A1 | 10/2003 |
| EP | 1468667 | A1 | 10/2004 |
| FR | 2823110 | A1 | 10/2002 |
| FR | 2838336 | A1 | 10/2003 |
| FR | 2842200 | A1 | 1/2004 |
| FR | 2854161 | A1 | 10/2004 |
| FR | 2910275 | A1 | 6/2008 |
| FR | 2932382 | A1 | 12/2009 |
| FR | 2944438 | A1 | 10/2010 |
| FR | 2944967 | A1 | 11/2010 |
| FR | 2961394 | A1 | 12/2011 |
| FR | 2975593 | A1 | 11/2012 |
| FR | 2994967 | A1 | 3/2014 |
| WO | 2006/057437 | A1 | 6/2006 |
| WO | 2007/090554 | A1 | 8/2007 |
| WO | 2009/150198 | A1 | 12/2009 |
| WO | 2010/070235 | A2 | 6/2010 |
| WO | 2011/161020 | A1 | 12/2011 |
| WO | 2013/132062 | A1 | 9/2013 |
| WO | 2015/036473 | A1 | 3/2015 |
| WO | 2015/036474 | A1 | 3/2015 |
| WO | 2015/036475 | A1 | 3/2015 |
| WO | 2015/036476 | A1 | 3/2015 |
| WO | 2018/046747 | A1 | 3/2018 |

OTHER PUBLICATIONS

English language Abstract for FR 2944967A1 (Nov. 5, 2010).
English language Abstract for FR 2842200A1 (Jan. 16, 2004).
English language Abstract for FR 2854161A1 (Oct. 29, 2004).
Office Action for counterpart application CN201480050160.5 dated Apr. 24, 2017.
Office Action for counterpart application CN201480050160.5 dated Nov. 27, 2017.
Final Office Action for counterpart U.S. Appl. No. 15/021,438, dated Dec. 28, 2017.
Final Office Action for counterpart U.S. Appl. No. 15/021,402, dated Sep. 28, 2017.
Office Action for counterpart U.S. Appl. No. 15/021,402, dated Apr. 6, 2017.
Office Action for counterpart U.S. Appl. No. 15/021,438, dated Jul. 18, 2017.
Non-Final Office Action for co-pending U.S. Appl. No. 15/021,438, dated May 17, 2019.
Non-Final Office Action for copending U.S. Appl. No. 14/383,993, dated Jul. 30, 2015 (now U.S. Pat. No. 10,085,931).
Final Office Action for copending U.S. Appl. No. 14/383,993, dated Apr. 8, 2016 (now U.S. Pat. No. 10,085,931).
Non-Final Office Action for copending U.S. Appl. No. 14/383,993, dated Aug. 22, 2017 (now U.S. Pat. No. 10,085,931).
International Search Report for counterpart Application No. PCT/EP2013/054720, dated Apr. 22, 2013.
Non-Final Office Action for copending U.S. Appl. No. 15/021,402, dated Jan. 8, 2019.
Fryxell, Anna K., "Get Your Straightest Hair Ever With These Tools," <https://www.newbeauty.com/blog/dailybeauty/6572-final-get-your-straightest-hair-ever-with-these-tools/>, Aug. 31, 2012.
Final Office Action for co-pending U.S. Appl. No. 15/021,438, dated Nov. 26, 2019.
Final Office Action for co-pending U.S. Appl. No. 15/021,402, dated Oct. 10, 2019.
Non-Final Office Action for copending U.S. Appl. No. 16/331,378, dated Sep. 2, 2020.
International Search Report and Written Opinion for counterpart Application No. PCT/EP2017/072828, dated Oct. 24, 2017.
Wing, R.E., et al., "Water soluble oxidized starches by peroxide reactive extrusion," Industrial Crops and Products, vol. 7, 1997, pp. 45-52.
Fredon, E. et al., "Hydrophobic films from maize bran hemicelluloses," Carbohydrate Polymers, vol. 49, No. 1, Jul. 1, 2002, pp. 1-12.
Karam, et al., "Rational Design of Sugar-Based-Surfactant Combined Catalysts for Promoting Glycerol as a Solvent," Chemistry A European Journal, vol. 14, No. 33, Nov. 17, 2008, pp. 10196-10200.
Final Office Action for copending U.S. Appl. No. 16/331,378, dated Mar. 23, 2021.

* cited by examiner

PROCESS FOR TREATING KERATIN FIBRES WITH A PYRIDINEDICARBOXYLIC ACID COMPOUND

CROSS REFERENCE TO RELATED APPLICATIONS

This is a national stage application of PCT/EP2014/069383, filed internationally on Sep. 11, 2014, which claims priority to French Application No. 1358764, filed on Sep. 12, 2013, both of which are incorporated by reference herein in their entireties.

The invention relates to a cosmetic process for treating sensitized keratin fibres, in particular human keratin fibres such as the hair, using a pyridinedicarboxylic acid compound.

Hair is generally damaged and embrittled by the action of chemical treatments such as dyeing, bleaching, permanent-waving, relaxing and repeated washing. Hair becomes sensitized and is thus damaged by these various treatments and may in the long run become dry, coarse, brittle or dull or split or limp.

Thus, to overcome these drawbacks, it is common practice to resort to hair treatments which involve compositions for conditioning the hair appropriately by giving it satisfactory cosmetic properties.

These haircare compositions may be, for example, conditioning shampoos, hair conditioners, masks or sera.

However, the conditioning effect obtained fades out in the course of successive shampoo washes and does not show satisfactory persistence on shampooing.

Patent application FR 2 838 336 discloses the use of pyridinedicarboxylic acid compounds for treating against hair loss.

There is thus a need for a process for treating sensitized keratin fibres, in particular sensitized hair, which is capable of durably conditioning sensitized keratin fibres, in particular for giving the hair good manageability and good sheen, the conditioning effect being persistent after one or more shampoo washes performed on the treated keratin fibres.

The Applicant has discovered that the application to sensitized keratin fibres, in particular sensitized hair, of a pyridinedicarboxylic acid compound as defined below makes it possible to obtain good hair-managing and sheen cosmetic properties, with a long-lasting effect, especially after shampooing one or more times.

Thus, one subject of the present invention is a process for treating sensitized keratin fibres, in particular sensitized hair, comprising the application to the keratin fibres of a cosmetic composition comprising a pyridinedicarboxylic acid compound as defined below.

In particular, hair treated via the process according to the invention remains managed since no presence of frizziness is observed. Thus, the hairs are aligned, smooth and disentangle easily, which makes them easier to comb.

Moreover, the treated hair is also shinier.

The process according to the invention has the advantage of giving good persistence of these hair-conditioning cosmetic properties after shampooing. Thus, the treated hair is durably conditioned.

A subject of the invention is also the use of a 2,4-pyridinedicarboxylic acid compound as defined below for improving the manageability and/or sheen of sensitized hair.

The 2,4-pyridinedicarboxylic acid compound used according to the invention is chosen from the compounds of formula (I) below:

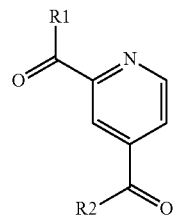

in which R1 and R2 represent, independently of each other, OH, OR', —NH2, —NHR', —NR'R", and R' and R" represent, independently of each other, a linear or branched, saturated or unsaturated C1-C18 alkyl, optionally substituted with at least one group chosen from OH, C1-C6 alkoxy, C1-C6 acyloxy, amino, (C1-C6)alkyloxycarbonyl or (C1-C6)alkylamino, or C6-C10 aryl, or salts thereof.

More particularly, R1 and R2 represent, independently of each other, OH or OR', R' represent, independently of each other, a linear or branched, saturated C1-C12 alkyl, optionally substituted with at least one OH, C1-C4 alkoxy, C1-C4 acyloxy, (C1-C4)alkyloxycarbonyl or (C1-C4)alkylamino group, or phenyl.

In a particularly preferred manner, R1 and R2 represent, independently of each other, OH or OR', and R' represent, independently of each other, a linear or branched, saturated C1-C6 alkyl, optionally substituted with at least one OH, C1-C4 alkoxy, C1-C4 acyloxy, (C1-C4)alkyloxycarbonyl or (C1-C4)alkylamino group, or phenyl, or a salt of one of these compounds.

The following 2,4-pyridinedicarboxylic acid derivatives are preferred in the context of the present invention:
- 2,4-pyridinedicarboxylic acid (compound 2) or a salt thereof, especially the disodium salt (compound 1)
- dimethyl 2,4-pyridinedicarboxylate (compound 3)
- diethyl 2,4-pyridinedicarboxylate (compound 4)
- 2-ethyl ester of 2,4-pyridinedicarboxylic acid (compound 8)
- 4-ethyl ester of 2,4-pyridinedicarboxylic acid (compound 10)
- diisopropyl 2,4-pyridinedicarboxylate (compound 6)
- 2,4-pyridinedicarboxylic acid di-n-propylamide
- 2-isopropyl ester of 2,4-pyridinedicarboxylic acid (compound 7)
- methyl glycolate ester of 2,4-pyridinedicarboxylic acid Compound 1

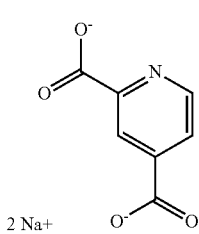

Compound 2

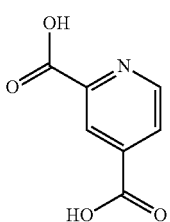

Compound 3

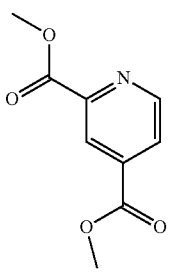

Compound 4

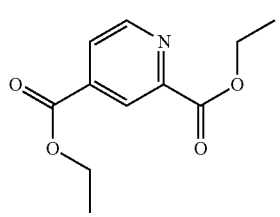

Compound 5

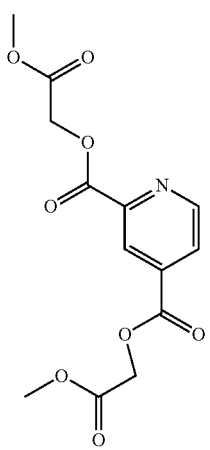

Compound 6

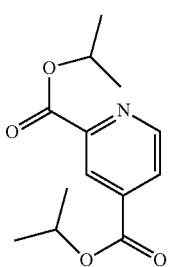

Compound 7

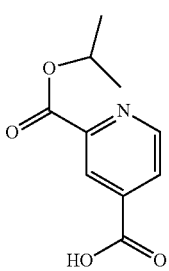

Compound 8

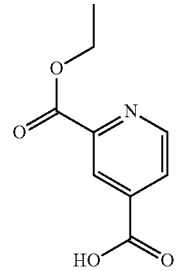

Compound 9

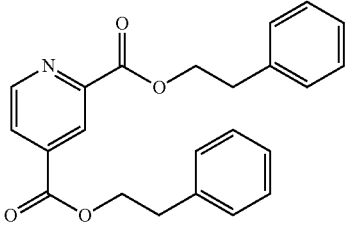

Compound 10

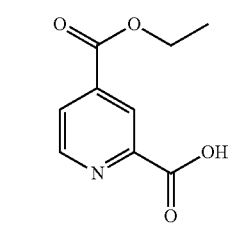

According to the invention, the term "salts of the compounds of formula (I)" means the organic or mineral salts of a compound of formula (I), these salts being physiologically acceptable. Mineral salts that may be mentioned include the sodium or potassium salts and also the salts of zinc ($Zn^{2+}$), of calcium ($Ca^{2+}$), of copper ($Cu^{2+}$), of iron ($Fe^{2+}$), of strontium ($Sr^{2+}$), of magnesium ($Mg^{2+}$), of manganese ($Mn^{2+}$); the hydroxides, the carbonates and the chlorides. Organic salts that may be mentioned include the triethanolamine, monoethanolamine, diethanolamine, hexadecylamine, N,N,N',N'-tetrakis(2-hydroxypropyl)ethylenediamine and tris(hydroxymethyl)aminomethane salts.

The compounds of formula (I) are known per se; they are especially described, along with their manufacture, in patent EP 1 352 629.

Advantageously, the 2,4-pyridinedicarboxylic acid derivative is present in the cosmetic composition used according to the invention in a content ranging from 0.1% to 10% by weight, preferably ranging from 0.5% to 8% by weight and more preferentially ranging from 0.5% to 6% by weight relative to the total weight of the composition.

The cosmetic composition used according to the invention contains a physiologically acceptable medium, i.e. a medium that is compatible with human keratin materials such as the skin (of the body, face, around the eyes or the scalp), the hair, the eyelashes, the eyebrows, bodily hair, the nails or the lips.

The physiologically acceptable medium of the composition used in the process according to the invention is advantageously an aqueous medium. It may consist, for example, of water or of a mixture of water and of at least one cosmetically acceptable organic solvent. Examples of organic solvents that may be mentioned include $C_2$-$C_4$ lower alcohols, such as ethanol and isopropanol; polyols, especially those containing from 2 to 6 carbon atoms, for instance glycerol, propylene glycol, butylene glycol, pentylene glycol, hexylene glycol, dipropylene glycol or diethylene glycol; polyol ethers, for instance 2-butoxyethanol, propylene glycol monomethyl ether and diethylene glycol monomethyl ether or monoethyl ether; and mixtures thereof.

Preferably, the cosmetic composition comprises from 50% to 99.5% by weight of water relative to the weight of the composition.

The composition used according to the invention may also contain one or more cosmetic additives chosen from non-ionic, anionic, cationic and amphoteric surfactants, vitamins and provitamins, including panthenol, sunscreens, fillers, dyestuffs, nacreous agents, opacifiers, sequestrants, film-forming polymers, plasticizers, thickeners, oils, antioxidants, antifoams, moisturizers, emollients, penetrants, fragrances and preserving agents.

The composition used according to the invention may be in any galenical form conventionally used for application to the hair and in particular in the form of aqueous solutions, aqueous-alcoholic solutions, oil-in-water (O/W), water-in-oil (W/O) or multiple (triple: W/O/W or O/W/O) emulsions, aqueous gels or aqueous-alcoholic gels. These compositions are prepared according to the usual methods. Preferably, the composition is in the form of an aqueous or aqueous-alcoholic solution or gel.

The process according to the invention may comprise a step of heating the keratin fibres to a temperature of at least 100° C., preferably ranging from 100 to 250° C. Preferably, the step of heating the keratin fibres is performed at a temperature ranging from 150 to 220° C., preferably ranging from 160° C. to 220° C., preferentially ranging from 160° C. to 200° C. and especially ranging from 170° C. to 190° C.

The heating step gives the hair good shaping.

The heating step is performed after the step of applying the composition comprising compound (I) to the keratin fibres.

This heating step is advantageously performed using an iron.

The heating step makes it possible to optimize the effects of the process, and especially to optimize the persistence of the cosmetic properties after shampooing one or more times.

For the purposes of the present invention, the term "iron" means a device for heating keratin fibres by placing the said fibres and the heating device in contact. The end of the iron which comes into contact with the keratin fibres generally has two flat surfaces. These two surfaces may be made of metal or ceramic. In particular, these two surfaces may be smooth or crimped or curved.

The heating step may be performed by means of a straightening iron, a curling iron, a crimping iron or a steam iron. Preferably, the heating step is performed using a straightening iron.

As examples of irons that may be used in the straightening process according to the invention, mention may be made of any type of flat iron, and in particular, in a nonlimiting manner, those described in U.S. Pat. Nos. 5,957,140 and 5,046,516.

The iron may be applied by successive separate strokes lasting a few seconds or by gradual movement or sliding along the locks of keratin fibres, especially of hair.

Preferably, the iron is applied in the process according to the invention by a continuous movement from the root to the end of the hairs, in one or more passes, in particular in two to twenty passes. The duration of each pass of the iron may last from 2 seconds to 1 minute.

Preferably, the step of heating the keratin fibres is performed for a time that may range from 2 seconds to 30 minutes, preferentially from 2 seconds to 20 minutes, better still from 2 seconds to 10 minutes, better still from 2 seconds to 5 minutes and even better still from 2 seconds to 2 minutes.

The process according to the invention may also comprise an additional step of drying the keratin fibres after the application of the composition comprising the pyridinedicarboxylic acid compound and before the step of heating the keratin fibres performed at a temperature of at least 100° C. The drying step may be performed using a hairdryer or a hood or by open drying. The drying step is advantageously performed at a temperature ranging from 20 to 70° C.

After the drying step, the keratin fibres may be optionally rinsed with water or washed with a shampoo. The keratin fibres are then optionally dried using a hairdryer or a hood or in the open air.

The treatment process according to the invention is performed on sensitized keratin fibres, especially sensitized hair, such as bleached, artificially dyed, relaxed or permanent-waved fibres.

The process according to the invention may be performed on keratin fibres, especially hair, which are dry or wet. Preferentially, the process is performed on dry keratin fibres, especially dry hair.

The cosmetic composition(s) used according to the invention are advantageously applied to the keratin fibres in an amount ranging from 0.1 to 10 grams and preferably from 0.2 to 5 grams of composition per gram of keratin fibres.

After application of the cosmetic composition to the keratin fibres, they may be manually dried to remove the excess composition or washed with water or with a shampoo.

After application to the keratin fibres of the composition comprising the pyridinedicarboxylic acid compound, and before performing the step of heating the keratin fibres, the applied composition may be left on for a time ranging from 1 to 60 minutes, preferably ranging from 2 to 50 minutes and preferentially ranging from 5 to 45 minutes. The composition may be left on at a temperature ranging from 15° C. to 45° C., preferably at room temperature (25° C.).

The treatment process according to the invention may be performed during and/or after an additional cosmetic process for treating the keratin fibres, for durably shaping (permanent-waving or relaxing) or dyeing keratin fibres.

In particular, the treatment process is performed as a post-treatment to a bleaching, artificial dyeing or relaxing process and/or a permanent-waving process so as to repair the said fibres.

The process according to the invention may be performed during a cosmetic treatment process so as to repair the said fibres.

The treatment process according to the invention is performed on sensitized keratin fibres such as bleached, dyed, relaxed or permanent-waved fibres.

As a variant, the treatment process may be performed during and/or after a cosmetic process for treating keratin fibres, in particular:
  (a) during and/or after a process of dyeing or a process of permanent-waving or a process of relaxing keratin fibres, and
  (b) after a process of bleaching keratin fibres.

According to one embodiment, the treatment process according to the invention is performed after a process of bleaching the keratin fibres.

The examples that follow are given as illustrations of the present invention. The amounts indicated in the examples are expressed as weight percentages.

EXAMPLE 1

Locks of sensitized type II frizzy hair were used (bleaching SA 20%). The composition to be evaluated is applied at a rate of 10 g of composition per gram of locks. Each composition evaluated was applied to three locks.

Compositions Prepared

| Compositions | A | X | Y |
|---|---|---|---|
| diethyl 2,4-pyridinedicarboxylate | 5 | | |
| Water/ethanol (50/50 weight/weight) | qs 100 | qs 100 | |
| Water | | | qs 100 |

Composition A was applied to locks of hair and then left on for 15 minutes at 40° C.

The locks were dried manually and then dried under a hood for 15 minutes at 60° C. The application of composition A was thus repeated five times in total, without rinsing, and, at the end of the treatment, shampooing was performed according to the following protocol:

The treated locks were washed with an aqueous solution containing 15% by weight of sodium lauryl ether sulfate at a rate of 0.4 g of shampoo per gram of hair, at a temperature of 38° C.

Moisten the lock for 5 seconds with water. Apply the shampoo, massaging the lock from the root to the end for 15 seconds. Rinse with water for 10 seconds. Dry manually. Dry the locks for 10 minutes per gram of hair at 60° C. with a hairdryer.

For comparative purposes, the same protocol was also performed on locks with, on the one hand, a placebo composition X and, on the other hand, composition Y containing only water (control lock).

The cosmetic properties of the locks after shampooing were then evaluated, especially the manageability of the locks and the sheen of the hair.

The following results were obtained:

| Type of lock of hair | Cosmetic properties after shampooing |
|---|---|
| Sensitized type II hair treated with composition (Y) (control) (Lock 1) | Dull, unmanageable lock |
| Sensitized type II hair treated with placebo composition (X) (Lock 2) | Duller, less manageable lock |
| Sensitized type II hair treated with composition (A) (Lock 3) | Shinier, more manageable lock |

The locks of hair were then classified as a function of their cosmetic properties (manageability, sheen) after having been shampooed.

| After shampooing | Lock 3 > Lock 1 > Lock 2 |
|---|---|

Lock 3 treated via the process according to the invention, and after having been shampooed, has better cosmetic properties in terms of manageability and sheen. These cosmetic properties thus have good persistence on shampooing.

EXAMPLE 2

Locks of sensitized type II frizzy hair were used (bleaching SA 20%). Composition A was applied to locks of hair and then left on for 15 minutes at 40° C.

The locks were dried manually and then dried under a hood for 15 minutes at 60° C.

The locks were combed before applying a straightening iron at a temperature of 180° C. by performing five continuous passes through the locks for 5 seconds.

For comparative purposes, the same protocol was also performed on locks with, on the one hand, a placebo composition X and, on the other hand, composition Y containing only water (control lock).

To evaluate the durable (persistent) nature of the cosmetic properties of the locks of hair, they were then washed with a shampoo according to the protocol described previously.

The cosmetic properties of the locks after shampooing was then evaluated, especially the soft feel, the manageability and shaping of the locks and the sheen of the hair.

The following results were obtained:

| Type of lock of hair | Cosmetic properties after shampooing |
|---|---|
| Type II natural hair treated with composition (Y) (control) + iron (Lock 11) | Coarse feel; dull, unmanageable lock |
| Type II natural hair treated with placebo composition (X) + iron (Lock 12) | Coarser feel; dull, more manageable lock |
| Type II natural hair treated with composition (A) + iron (Lock 13) | Softer feeling, more manageable lock, sheen improved. Better shaping |

The locks of hair were then classified as a function of their cosmetic properties (soft, pleasant cosmetic feel, manageability, shaping and sheen) after having been shampooed.

| After shampooing | Lock 13 > Lock 11 > Lock 12 |
|---|---|

Lock 13 treated via the process according to the invention, and after having been shampooed, has better cosmetic properties in terms of soft feel, manageability and shaping, and also sheen. These cosmetic properties thus have good persistence on shampooing.

The invention claimed is:

1. A process for protecting or conditioning bleached, artificially dyed, relaxed and/or permanent-waved keratin fibers, the process comprising:
   applying to the bleached, artificially dyed, relaxed and/or permanent-waved keratin fibers a cosmetic conditioning composition comprising a pyridinedicarboxylic acid compound of formula (I) or salts thereof:

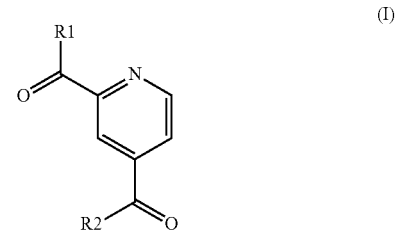

(I)

wherein:
R1 and R2, independently, are chosen from OH, OR', —NH2, —NHR', or —NR'R",
wherein R' and R", independently, are chosen from a linear or branched, saturated or unsaturated C1-C18 alkyl, optionally substituted with at least one group chosen from OH, C1-C6 alkoxy, C1-C6 acyloxy, amino, (C1-C6)alkyloxycarbonyl, (C1-C6)alkylamino, or C6-C10 aryl, wherein applying the pyridinedicarboxylic acid compound of formula (I) comprises applying the cosmetic conditioning composition comprising the compound of formula (I) in an amount ranging from about 0.5% to 6% by weight, relative to the total weight of the cosmetic conditioning composition; and heating the keratin fibers with an iron at a temperature of at least 170° C. after applying the cosmetic conditioning composition comprising the pyridinedicarboxylic acid compound of formula (I), and wherein the cosmetic conditioning composition does not comprise oxidized polysaccharides.

2. The process according to claim 1, wherein R1 and R2, independently, are chosen from OH or OR'.

3. The process according to claim 1, wherein R', independently, is chosen from a linear or branched, saturated C1-C12 or C1-C6 alkyl, optionally substituted with at least one OH, C1-C4 alkoxy, C1-C4 acyloxy, (C1-C4)alkyloxycarbonyl, (C1-C4)alkylamino, or phenyl.

4. The process according to claim 1, wherein the pyridinedicarboxylic acid compound of formula (I) is chosen from:

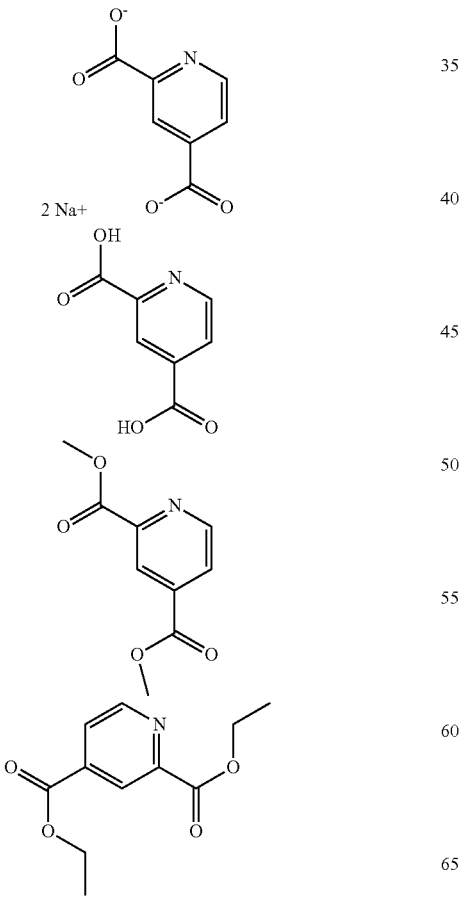

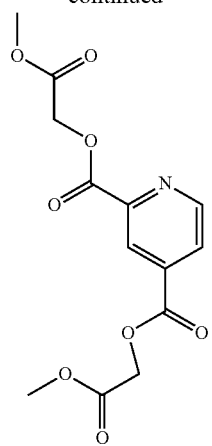

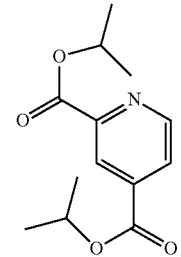

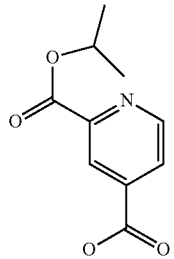

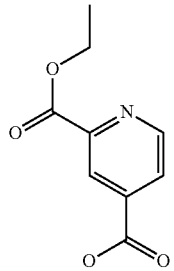

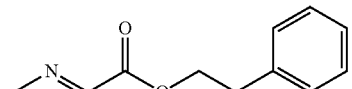

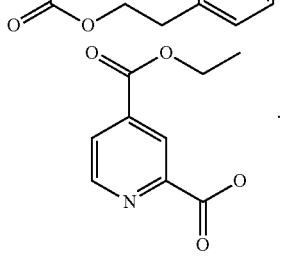

5. The process according to claim 1, wherein the heating step is performed at a temperature ranging from 170° C. to about 250° C.

6. The process according to claim 1, wherein the heating step is performed at a temperature ranging from 170° C. to about 200° C.

7. The process according to claim 1, further comprising drying the keratin fibers after the application of the cosmetic conditioning composition comprising the pyridinedicarboxylic acid compound of formula (I), and before the step of heating the keratin fibers performed at a temperature of at least 170° C.

8. The process according to claim 7, wherein the drying is performed at a temperature ranging from about 20° C. to about 70° C.

9. The process according to claim 1, wherein after application to the keratin fibers of the cosmetic conditioning composition comprising the pyridinedicarboxylic acid compound of formula (I), and before heating the keratin fibers, the applied cosmetic conditioning composition is left on for a time ranging from about 1 to about 60 minutes.

10. The process according to claim 1, wherein the process is performed on hair.

11. The process according to claim 1 performed on hair, wherein the heating is performed by applying a straightening iron, in a substantially continuous movement from the root to the end of the hair, in at least one pass.

12. The process according to claim 1, wherein the cosmetic conditioning composition comprising the pyridinedicarboxylic acid compound of formula (I) further comprises a physiologically acceptable aqueous medium.

13. A process for improving the manageability and/or sheen of bleached, artificially dyed, relaxed and/or permanent-waved keratin fibers, the process comprising:

applying to the bleached, artificially dyed, relaxed and/or permanent-waved keratin fibers a cosmetic composition comprising a pyridinedicarboxylic acid compound of formula (I) or salts thereof:

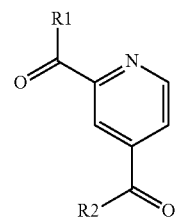

wherein:
R1 and R2, independently, are chosen from OH, OR', —NH2, —NHR', or —NR'R",
wherein R' and R", independently, are chosen from a linear or branched, saturated or unsaturated C1-C18 alkyl, optionally substituted with at least one group chosen from OH, C1-C6 alkoxy, C1-C6 acyloxy, amino, (C1-C6)alkyloxycarbonyl, (C1-C6)alkylamino, or C6-C10 aryl, wherein applying the pyridinedicarboxylic acid compound of formula (I) comprises applying the cosmetic composition comprising the compound of formula (I) in an amount ranging from about 0.5% to 6% by weight, relative to the total weight of the cosmetic composition; and heating the keratin fibers with an iron at a temperature of at least 170° C. after applying the cosmetic composition comprising the pyridinedicarboxylic acid compound of formula (I), and wherein the cosmetic composition does not comprise oxidized polysaccharides.

14. The process according to claim 13, further comprising at least one of:

drying the keratin fibers after the application of the cosmetic composition comprising the pyridinedicarboxylic acid compound of formula (I); or leaving the applied cosmetic composition on the keratin fibers for a time ranging from about 1 to about 60 minutes.

\* \* \* \* \*